US011589752B2

(12) United States Patent
Nagae (10) Patent No.: US 11,589,752 B2
(45) Date of Patent: Feb. 28, 2023

(54) PHOTOACOUSTIC APPARATUS AND OBJECT INFORMATION ACQUIRING METHOD

(71) Applicant: CANON KABUSHIKI KAISHA, Tokyo (JP)

(72) Inventor: Kenichi Nagae, Yokohama (JP)

(73) Assignee: CANON KABUSHIKI KAISHA, Tokyo (JP)

(*) Notice: Subject to any disclaimer, the term of this patent is extended or adjusted under 35 U.S.C. 154(b) by 505 days.

(21) Appl. No.: 16/383,785

(22) Filed: Apr. 15, 2019

(65) Prior Publication Data

US 2019/0320907 A1 Oct. 24, 2019

(30) Foreign Application Priority Data

Apr. 20, 2018 (JP) .............................. JP2018-081436

(51) Int. Cl.
| | | |
|---|---|---|
| *A61B 5/00* | (2006.01) | |
| *G01N 21/17* | (2006.01) | |
| *G01N 29/24* | (2006.01) | |
| *A61B 5/145* | (2006.01) | |

(52) U.S. Cl.
CPC ............ *A61B 5/0095* (2013.01); *A61B 5/004* (2013.01); *A61B 5/14542* (2013.01); *G01N 21/1702* (2013.01); *G01N 29/2418* (2013.01); *G01N 2021/1706* (2013.01)

(58) Field of Classification Search
CPC ... A61B 5/0095; A61B 5/14542; A61B 5/004; G01N 21/1702; G01N 29/2418; G01N 2021/1706
See application file for complete search history.

(56) References Cited

U.S. PATENT DOCUMENTS

| | | |
|---|---|---|
| 8,396,534 B2 | 3/2013 | Fukutani et al. |
| 8,747,318 B2 | 6/2014 | Shiina et al. |
| 8,784,317 B2 | 7/2014 | Taki et al. |
| 8,905,931 B2 | 12/2014 | Baba et al. |
| 8,929,174 B2 | 1/2015 | Yoda et al. |
| 8,998,814 B2 | 4/2015 | Oikawa et al. |

(Continued)

FOREIGN PATENT DOCUMENTS

| | | |
|---|---|---|
| JP | 2016-059768 | 4/2016 |
| JP | 2016-137053 A | 8/2016 |

*Primary Examiner* — Sean D Mattson
(74) *Attorney, Agent, or Firm* — Venable LLP (57) ABSTRACT

A photoacoustic apparatus includes a light source configured to generate a plurality of pulsed lights in different wavelengths, an irradiation optical system configured to irradiate an object with the pulsed light from the light source and configured to irradiate the object in different irradiation positions along a rotational trajectory during a rotational scanning period in a corresponding wavelength, and a probe configured to receive photoacoustic wave from the object in response to each pulsed light irradiation in the different irradiation positions and to convert the received photoacoustic wave into an electric signal. The irradiation optical system is moved to irradiate the object with a first wavelength in a plurality of times during a first rotational scanning period and irradiate the object with a second wavelength in a plurality of times during a second rotational scanning period after the first rotational scanning period.

20 Claims, 6 Drawing Sheets

(56) References Cited

U.S. PATENT DOCUMENTS

| | | |
|---|---|---|
| 9,063,220 B2 | 6/2015 | Yoda et al. |
| 9,110,155 B2 | 8/2015 | Nagae |
| 9,116,225 B2 | 8/2015 | Yoda et al. |
| 9,448,100 B2 | 9/2016 | Nagae et al. |
| 9,482,646 B2 | 11/2016 | Nagae et al. |
| 9,572,498 B2 | 2/2017 | Nagae et al. |
| 9,683,971 B2 | 6/2017 | Taki et al. |
| 9,757,093 B2 | 9/2017 | Taki et al. |
| 10,088,560 B2 | 10/2018 | Nagae et al. |
| 10,189,049 B2 | 1/2019 | Torashima et al. |
| 2012/0259198 A1 | 10/2012 | Nagae et al. |
| 2014/0051970 A1 | 2/2014 | Ebisawa et al. |
| 2014/0206960 A1* | 7/2014 | Nagae ............... A61B 5/0091 600/310 |
| 2014/0318255 A1 | 10/2014 | Torashima et al. |
| 2016/0066792 A1* | 3/2016 | Oyama ............... A61B 5/0095 600/407 |
| 2016/0213259 A1* | 7/2016 | Wanda ............... A61B 5/708 |
| 2016/0296206 A1 | 10/2016 | Ebisawa et al. |
| 2016/0331347 A1 | 11/2016 | Ebisawa et al. |
| 2016/0345886 A1 | 12/2016 | Wang et al. |
| 2017/0052254 A1* | 2/2017 | Tateyama ............ G01S 15/8993 |
| 2017/0238862 A1* | 8/2017 | Fukutani ............ A61B 5/0095 |
| 2017/0265750 A1 | 9/2017 | Iizuka et al. |
| 2017/0332909 A1 | 11/2017 | Nagae et al. |
| 2018/0028066 A1 | 2/2018 | Urano et al. |
| 2018/0085005 A1* | 3/2018 | Umezawa ............ G06T 5/006 |
| 2018/0103849 A1 | 4/2018 | Iizuka et al. |

* cited by examiner

PHOTOACOUSTIC APPARATUS AND OBJECT INFORMATION ACQUIRING METHOD

BACKGROUND OF THE INVENTION

Field of the Invention

The present invention relates to a photoacoustic apparatus.

Description of the Related Art

As a technique to image functional information on the inside of an object, such as structural information and physiological information, photoacoustic tomography (PAT) is known.

If a living body, which is an object, is irradiated with light, such as laser light, an acoustic wave (typically an ultrasonic wave) is generated when the light is absorbed by a biological tissue inside the object. This phenomenon is called a "photoacoustic effect" and the acoustic wave generated by the photoacoustic effect is called a "photoacoustic wave". The absorption rate of optical energy differs depending on the tissue constituting the object, hence the sound pressure of the generated photoacoustic wave also differs depending on the tissue. With PAT, a generated photoacoustic wave is received by a probe, and the received signal is mathematically analyzed so as to acquire characteristic information inside the object.

Further, in photoacoustic tomography, an object is irradiated with lights having mutually different wavelengths, and the absorption coefficient of the light is determined for each wavelength, whereby concentration related distribution of a substance (distribution of values related to the concentration of a substance) existing in the object can be acquired.

As a technique related to this, Japanese Patent Application Publication No. 2016-59768, for example, discloses a photoacoustic apparatus which irradiates an object with lights having a plurality of wavelengths, and acquires functional information inside the object, such as the oxygen saturation degree.

SUMMARY OF THE INVENTION

In the apparatus according to Japanese Patent Application Publication No. 2016-59768, the wavelength of light is switched while moving the probe, and a different position on the object is irradiated with light having a different wavelength. However, according to this configuration, the light intensity distribution in the object changes depending on the wavelength, hence the functional information, such as the oxygen saturation degree, may not be acquired accurately.

With the foregoing problem of the prior art in view, it is an object of the present invention to improve the measurement accuracy of a photoacoustic apparatus which uses lights having a plurality of wavelengths.

It is provided with a view to achieving one aspect as describe above a photoacoustic apparatus, including:

a light source configured to generate a plurality of pulsed lights in different wavelengths;

an irradiation optical system optically coupled to the light source, configured to irradiate an object with the pulsed light from the light source and configured to irradiate the object in different irradiation positions along a rotational trajectory during a rotational scanning period of time in a corresponding wavelength; and a probe configured to receive photoacoustic wave from the object in response to each light irradiation in the different irradiation positions and to convert the received photoacoustic wave into an electric signal, wherein the irradiation optical system is moved to irradiate the object with a first wavelength in a plurality of times during a first rotational scanning period of time and irradiate the object with a second wavelength in a plurality of times during a second rotational scanning period of time after the first rotational scanning period of time.

It is also provided with a view to achieving one aspect as describe above a method of acquiring object information, including:

irradiating an object with pulsed light from a light source configured to generate a plurality of pulsed lights in different wavelengths in different irradiation positions along a rotational trajectory during a rotational scanning period of time in a corresponding wavelength;

receiving photoacoustic wave from the object in response to each light irradiation in the different irradiation positions; and converting the received photoacoustic wave into an electric signal, wherein the irradiating irradiates the object with a first wavelength in a plurality of times during a first rotational scanning period of time and irradiates the object with a second wavelength in a plurality of times during a second rotational scanning period of time after the first rotational scanning period of time.

According to the present invention, the measurement accuracy can be improved in a photoacoustic apparatus which uses lights having a plurality of wavelengths.

Further features of the present invention will become apparent from the following description of exemplary embodiments with reference to the attached drawings.

DESCRIPTION OF THE EMBODIMENTS

Embodiments of the present invention will be described with reference to the drawings. Dimensions, materials, shapes and relative positions of components described below should be appropriately changed depending on the configurations and various conditions of the apparatus to which the invention is applied. Therefore, the following description is not intended to limit the scope of the invention.

The present invention relates to a technique to detect an acoustic wave propagating from an object, and generate and acquire the characteristic information inside the object. This means that the present invention is regarded as a photoacoustic apparatus or a control method thereof. The present invention is also regarded as a program which causes the apparatus, equipped with such hardware resources as a CPU and memory, to execute this method, or a computer readable non-transitory storage medium storing this program.

The photoacoustic apparatus according to the embodiments is an apparatus utilizing a photoacoustic effect, that is, an acoustic wave, generated inside an object (e.g. breast, face, palm) by irradiating the object with light (electromagnetic wave), is received, and characteristic information of the object is acquired as the image data. In this case, the characteristic information refers to information on the characteristic values corresponding to a plurality of positions inside the object respectively, and these characteristic values are generated using the received signals, which are acquired by receiving a photoacoustic wave.

The characteristic information acquired by the photoacoustic measurement refers to the values reflecting the absorption rate of the optical energy. For example, the characteristic information includes: a generation source of an acoustic wave which is generated by the pulsed light irradiation; an initial sound pressure inside the object; an optical energy absorption density and an absorption coefficient derived from the initial sound pressure; and a concentration of a substance constituting a tissue.

Based on photoacoustic waves that are generated by lights having a plurality of different wavelengths, information, such as the concentration of a substance constituting the object, can be acquired. This information may be an oxygen saturation degree, a value generated by weighting the oxygen saturation degree by intensity (e.g. absorption coefficient), a total hemoglobin concentration, an oxyhemoglobin concentration or deoxyhemoglobin concentration. This information may also be a glucose concentration, a collagen concentration, a melanin concentration, or a volume percentage of fat or water.

In the embodiments described below, it is assumed the use of a photoacoustic imaging apparatus configured to acquire data on distribution and profiles of blood vessels inside the object and data on the oxygen saturation distribution in the blood vessels, by irradiating the object with light having a wavelength which is determined based on the assumption that the absorber is hemoglobin, and image this data.

Based on the characteristic information at each position inside the object, a two-dimensional or three-dimensional characteristic information distribution is acquired. The distribution data can be generated as image data. The characteristic information may be determined, not as numeric data, but as distribution data at each position inside the object. In other words, such distribution information as the initial sound pressure distribution, the energy absorption density distribution, the absorption coefficient distribution, and the oxygen saturation distribution may be acquired.

The "acoustic wave" in the present description is typically an ultrasonic wave, including an elastic wave called a "sound wave" or a "photoacoustic wave". An electric signal, converted from the acoustic wave by a probe or the like, is called an "acoustic signal". Such phrases as "ultrasonic wave" or "acoustic wave" in this description, however, are not intended to limit the wavelengths of these elastic waves. An acoustic wave generated due to the photoacoustic effect is called a "photoacoustic wave" or a "light-induced ultrasonic wave". An electric signal, which originates from a photoacoustic wave, is called a "photoacoustic signal". In this description, the photoacoustic signal includes both an analog signal and a digital signal. The distribution data is also called "photoacoustic image data" or "reconstructed image data".

The photoacoustic apparatus according to the embodiments is an apparatus that irradiates an object with a pulsed light, and receives a photoacoustic wave generated inside the object, so as to generate information related to the optical characteristic inside the object.

Embodiment 1

Figure 1:
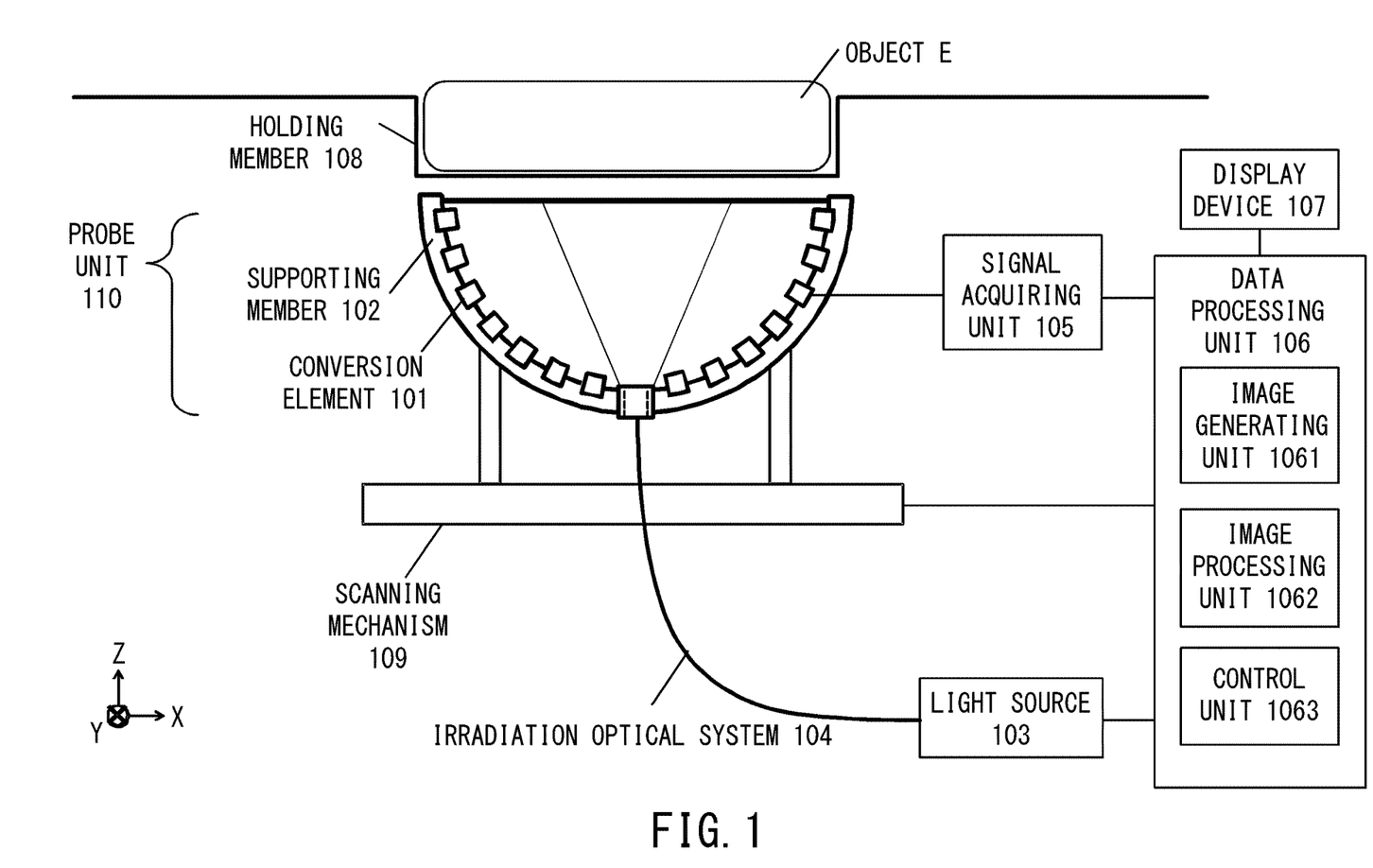
FIG. 1 is a diagram depicting a configuration of a photoacoustic apparatus according to Embodiment 1.

FIG. 1 is a diagram depicting a configuration of a photoacoustic apparatus according to Embodiment 1. The photoacoustic apparatus according to Embodiment 1 is constituted of a probe unit 110, a light source 103, an irradiation optical system 104, a signal acquiring unit 105, a data processing unit 106, a display device 107, a holding member 108 and a scanning mechanism 109.

The probe unit 110 includes a plurality of conversion elements 101 and a support member 102. The data processing unit 106 includes an image generating unit 1061, an image processing unit 1062 and a control unit 1063.

The probe unit 110 includes the irradiation optical system 104 optically connected the light source 103. The irradiation optical system 104 irradiates an object with pulsed light from the light source 103 and receives a generated acoustic wave from the object. The probe unit 110 is configured by disposing a plurality of (e.g. 512) conversion elements 101 in a spiral, on an inner surface of the support member 102 which has a hemispherical shape. Further, an opening, through which the pulsed light emitted from the later mentioned light source 103 transmits, is disposed at the bottom of the support member 102. In other words, the probe unit 110 includes the probe array including the plurality of conversion elements 101 and the irradiation optical system 104 optically connected the light source 103.

The support member 102 is an approximately hemispherically shaped container which supports the plurality of conversion elements 101. In Embodiment 1, the plurality of conversion elements 101 are disposed on the inner surface of the hemisphere, and an opening, to allow the pulsed light to transit through, is created at the bottom (pole) of the hemisphere, to which the later mentioned irradiation optical system 104 is connected. Acoustic matching materials (e.g. water) may be stored inside the hemisphere. To support these members, it is preferable that the support member 102 is constituted of a metal material or the like which has high mechanical strength. It is even more preferable that the support member 102 is configured to have such mechanical strength that the position of the probe unit 110 is maintained when the scanning mechanism 109 moves the probe unit 110.

The conversion element 101 is a unit that receives an acoustic wave emitted from inside the object in response to each pulsed light irradiation in different irradiation positions, and converts the received acoustic wave into an electric signal (hereafter photoacoustic signal). The conversion element is also called a probe, an acoustic wave detecting element, an acoustic wave detector, an acoustic wave receiver or a transducer.

An acoustic wave generated from a living body is an ultrasonic wave in the 100 KHz to 100 MHz range, hence an element that can receive this frequency band is used for the acoustic wave detecting element. In concrete terms, a transducer utilizing a piezoelectric phenomenon, a transducer utilizing the resonance of light, a transducer utilizing the change in capacitance or the like can be used.

It is preferable that the acoustic wave detecting element has high sensitivity and can handle a wide frequency band. In concrete terms, a piezoelectric element using lead zirconate titanate (PZT) or an element using a high polymer piezoelectric material such as polyvinylidene fluoride (PVDF), a capacitive micro-machine ultrasonic transducer (CMUT), a Fabry-Perot interferometer or the like may be used. The acoustic wave detecting element, however, is not limited to the above, but may be any element as long as the functions of the probe can be performed.

The plurality of conversion elements 101 are arranged in an array on the hemispheric surface, so that the direction of each element in which the receiving sensitivity is the highest (directivity axis) is directed to a predetermined region which includes the center of the curvature of the hemisphere and the vicinity thereof. By disposing the plurality of conversion elements 101 like this, high resolution can be implemented at the center of the curvature of the hemisphere. In this description, such a region where resolution is enhanced is called a "high resolution region". In Embodiment 1, the high resolution region is a region from a point at which the highest resolution is acquired to a point at which a resolution half that of the highest resolution is acquired. In Embodiment 1, the center of the hemispheric support member 102 is a position at which the highest receiving sensitivity is acquired, and the high resolution region is a spherical region which spreads isotropically from the center of the hemisphere.

By disposing the plurality of conversion elements 101 multi-dimensionally like this, the acoustic wave can be simultaneously received at a plurality of positions, which decreases the measurement time. The shape of the support member 102 is not limited to a hemisphere, as long as the direction of the high receiving sensitivity of each of the conversion elements 101 can be concentrated to a predetermined region. For example, the support member 102 may be ellipsoid-shaped sectioned at an arbitrary cross-section, or may be polyhedron-shaped.

The probe unit 110 can be moved in three-dimensional directions by the scanning mechanism 109. Thereby the pulsed light irradiating position and the acoustic wave receiving position can be relatively moved with respect to the object. In other words, the optical system 104 is moved to irradiate the object with a first wavelength in a plurality of times during a first rotational scanning period of time and irradiate the object with a second wavelength in a plurality of times during a second rotational scanning period of time after the first rotational scanning period of time. The scanning mechanism 109 may have a guide mechanism, a driving mechanism, a scanning position sensor and the like in the three directions of the X, Y and Z axes respectively.

The light source 103 is a unit configured to generate a pulsed light with which an object is irradiated. The light source 103 is preferably a laser light source in order to generate high power, but a light-emitting diode or a flash lamp may be used instead of laser. In the case of using a laser as the light source, various lasers, such as a solid-state laser, a gas las, a dye laser and a semiconductor laser can be used.

The wavelength of the pulsed light is preferably a specific wavelength that is absorbed by a specific component, out of the components constituting the object, and is also a wavelength by which the pulsed light can propagate into the object. In concrete terms, a wavelength at least 500 nm and not more than 1200 nm is preferable.

To effectively generate a photoacoustic wave, the object is required to be irradiated with the pulsed light for a sufficiently short time in accordance with the thermal characteristic of the object. When the object is a living body, as in the case of Embodiment 1, the pulse width of the pulsed light that is generated from the light source is preferably 10 to 100 nanoseconds.

The timing, waveform, intensity and the like of the pulsed light irradiation are controlled by the later mentioned data processing unit 106 (control unit 1063).

The laser used for the light source 103 is preferably a laser which has high power, and of which wavelength can be continuously changed, such as an Nd:YAG-excited Ti:sa laser and an alexandrite laser. In the case of irradiations of lights having a plurality of wavelengths, the light source 103 may include a plurality of single-wavelength laser of which wavelengths are different from one another.

The irradiation optical system 104 is a member which transmits the pulsed light emitted from the light source. The pulsed light emitted from the light source is guided to the object while being processed to be a predetermined pulsed light distribution profile by such optical components as a lens and mirror, and the object is irradiated with the pulsed light. The pulsed light may be propagated by an optical waveguide, such as optical fiber. In other words, the pulsed light distribution profile is called as a light irradiation pattern or a light irradiation distribution.

The irradiation optical system 104 may have a configuration where a plurality of hollow waveguides are connected by each joint including a mirror, and light is guided through the waveguides. The irradiation optical system 104 may have a configuration to guide the pulsed light by propagating the pulsed light in a space using such an optical element as a mirror and lens.

The irradiation optical system 104 may include such optical components as a lens, a mirror, a prism, an optical fiber, a diffusion plate, a shutter and a filter. Any optical component may be used for the optical system, as long as the object is irradiated with the pulsed light emitted from the light source 103 in a desired profile. In terms of safety of a living body and expanding the diagnostic region, it is preferable to expand the pulsed light to a certain area, rather than condensing the pulsed light by a lens.

The signal acquiring unit 105 is a unit that amplifies an electric signal acquired by the conversion element 101, and converts the amplified electric signal into a digital signal.

The signal acquiring unit 105 may be configured by an amplifier that amplifies a received signal, an A/D converter that converts the received analog signal into a digital signal, a memory (e.g. FIFO) that stores the received signal, and an arithmetic circuit (e.g. FPGA chip). Further, the signal acquiring unit 105 may be configured by a plurality of processors and arithmetic circuits.

The data processing unit 106 includes: a unit that reconstructs an image using digital signals outputted from the signal acquiring unit 105 (image generating unit 1061); a unit that processes an image (image processing unit 1062); and a unit that controls each composing element of the photoacoustic apparatus (control unit 1063).

The data processing unit 106 may be a computer constituted of a CPU, a RAM, a non-volatile memory and a control port. In this case, the program stored in the non-volatile memory is executed by the CPU, whereby control is performed. The data processing unit 106 may be implemented by a general purpose computer or a dedicated workstation. The unit which plays an arithmetic function of the data processing unit 106 may be configured by a processor (e.g. CPU, GPU) and an arithmetic circuit (e.g. FPGA chip). These units may be a single processor or a single arithmetic circuit, or may be constituted of a plurality of processors and arithmetic circuits.

The image generating unit 1061 calculates the initial sound pressure distribution p (r) of the photoacoustic wave inside the object, based on the converted digital signal (photoacoustic signal) using such a method as a filter back projection (FBP). In FBP, the image is reconstructed using the following formula (1). Here $dS_0$ denotes a size of the detector, $S_0$ denotes an opening size used for the reconstruction, pd (r, t) denotes a signal received by the plurality of conversion elements, t denotes the reception time, and $r_0$ denotes the positions of the plurality of composing elements.

[Math. 1]

$$p(r) = -\frac{1}{2\pi} \int_{S_0} \int \frac{dS_0}{r_0^2} \left[ t \frac{\partial p_d(r_0, t)}{\partial t} + 2 p_d(r_0, t) \right]_{t=|r-r_0|/c} \quad \text{Formula (1)}$$

The image processing unit 1062 performs image processing on image data generated by the image reconstruction processing. For example, a gain correction processing, a noise suppression processing using a Gaussian filter or a median filter, generation of a maximum intensity projection (MIP) image, coloring based on the direction and distance, or generation of a projected image by changing the saturation and lightness may be performed.

Further, the functional information in the object may be calculated using a plurality of reconstruction data so as to generate a corresponding image. An image generated like this can also be the target of the above-mentioned image processing. Furthermore, image processing to emphasize a region specified by the operator may be performed. The processed image is outputted to the display device 107.

In other words, the image generating unit 1061 is configured to generate a first image based on an electric signal from the probe in association with a first photoacoustic wave from the object in response to a first pulsed light irradiation with the pulsed light in the first wavelength, generate a second image based on an electric signal from the probe in association with a second photoacoustic wave from the object in response to a second pulsed light irradiation with the pulsed light in the second wavelength, and generate a third image representing functional information on an inside of the object based on the first image and the second image.

The control unit 1063 issues instructions on control of the apparatus in general, such as control of the pulsed light irradiation of the object, control of receiving the acoustic wave and photoacoustic signal, and control of moving the probe unit.

In Embodiment 1, the image generating unit 1061, the image processing unit 1062 and the control unit 1063 are implemented by common hardware, but may be implemented as separate hardware.

The unit which plays a storage function of the data processing unit 106 may be a non-transitory storage medium (e.g. ROM, magnetic disk, flash memory) or a volatile medium (e.g. RAM). A storage medium storing programs is a non-transitory storage medium. Each of these units may be constituted of one storage medium or may be constituted of a plurality of storage media.

The display device 107 is a unit that displays information acquired by the data processing unit 106 and the processed information thereof, and is typically a display. The display device 107 may be constituted of a plurality of devices, or may be a single device which has a plurality of display portions where parallel display can be performed. The display device 107 may include an input unit to receive instructions from the operator, such as a touch panel. The input unit may be disposed separately from the display device 107.

The holding member 108 is a member that holds an object. In Embodiment 1, the object is inserted in the positive direction on the Z axis in FIG. 1, and is held in a state of being in contact with the holding member 108. It is preferable that the holding member 108 is constituted of a material having strength to support the object and a characteristic to transmit light and acoustic waves, such as polyethylene terephthalate. If necessary, the acoustic matching material may be stored inside the holding member 108.

The scanning mechanism 109 is a unit that moves the probe unit 110, which includes the conversion elements 101 and the support member 102, relative to the object. In Embodiment 1, the probe unit 110 is moved, but the scanning mechanism 109 may have a configuration in which the object is moved with fixing the probe unit 110. Further, the scanning mechanism 109 may have a configuration in which both the probe unit 110 and the object are moved. The configuration of the scanning mechanism 109 is not limited, as long as the relative positions of the probe unit 110 and the object can be changed.

In Embodiment 1, the scanning mechanism 109 includes a movable stage, so that the probe unit 110 can be moved two-dimensionally (XY directions) or three-dimensionally (XYZ directions).

In other words, in Embodiment 1, the optical system 104 is moved, but the scanning mechanism 109 may have a configuration in which the object is moved with fixing the optical system 104. Further, the scanning mechanism 109 may have a configuration in which both the optical system 104 and the object are moved. The configuration of the scanning mechanism 109 is not limited, as long as the relative positions of the optical system 104 and the object can be changed.

In Embodiment 1, the scanning mechanism 109 includes a movable stage, so that the optical system 104 can be moved two-dimensionally (XY directions) or three-dimensionally (XYZ directions).

A method of measuring a living body (object) using the photoacoustic apparatus according to Embodiment 1 will be described next.

First an object is irradiated with a pulsed light emitted from the light source 103 via the irradiation optical system 104. When a part of the energy of the pulsed light propagating inside the object is absorbed by a light absorber (e.g. blood), an acoustic wave is generated from this light absorber by thermal expansion. If a cancer exists in the living body, light is uniquely absorbed by the blood in the newly generated blood vessels of the cancer in the same manner as the case of the blood in a normal region, and an acoustic wave is generated. The photoacoustic wave generated inside the living body is received by the conversion elements 101.

In Embodiment 1, the object is irradiated with the pulsed light and the acoustic wave is acquired while the scanning mechanism changes the relative positional relationship between the support member 102 and the object. In other words, the photoacoustic signal can be acquired while different positions on the object is irradiated with the pulsed light.

Figure 2A:
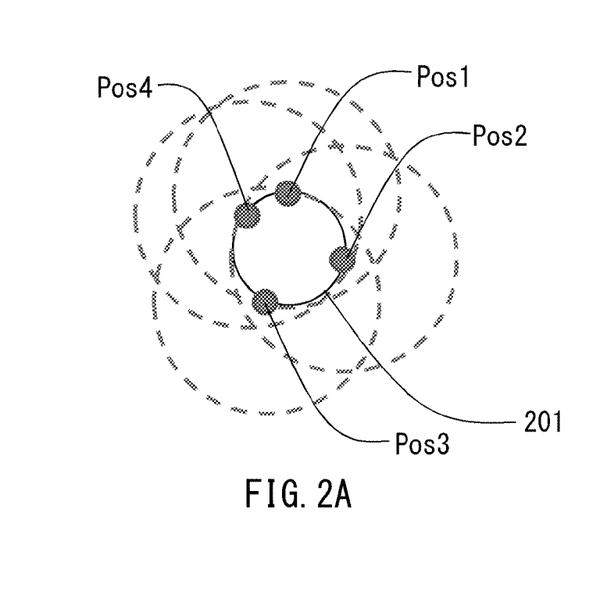
FIG. 2A and FIG. 2B indicate diagrams depicting movement of a probe unit according to Embodiment 1.
Figure 2B:
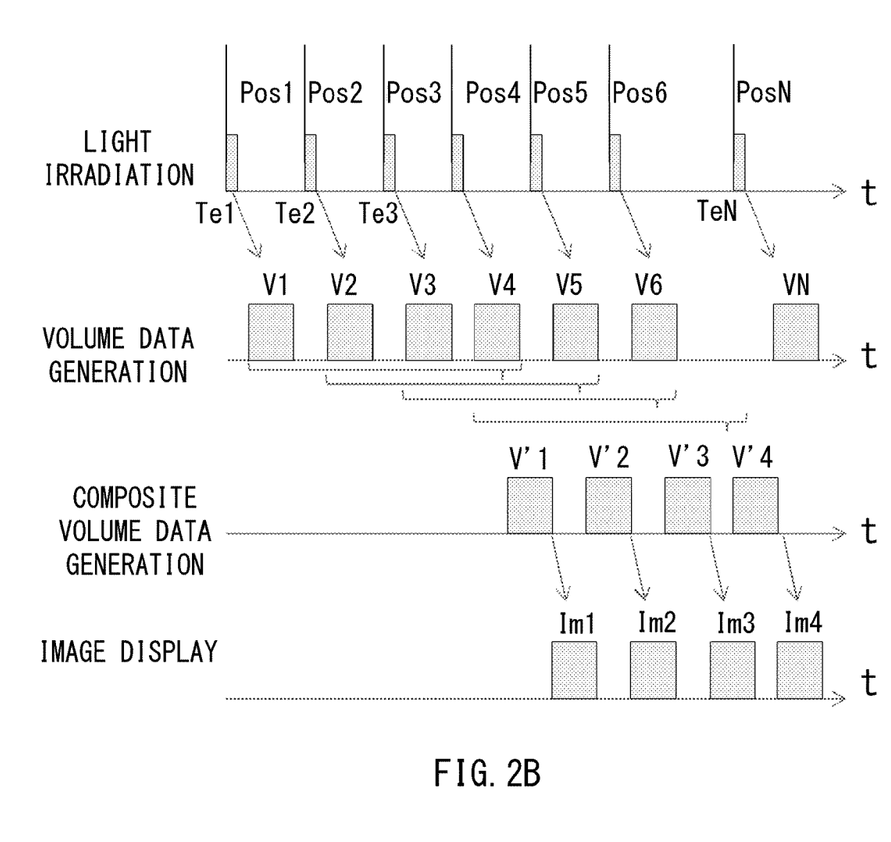

FIG. 2A is a schematic diagram depicting a movement of the probe unit 110 in the XY plane according to Embodiment 1. FIG. 2B is a diagram depicting the timings of the pulsed light irradiation, the volume data generation and the image display.

The reference number 201 in FIG. 2A indicates the solid line, which is the trajectory of the center point of the high resolution region when the probe unit 110 moves in the XY plane. In other words, FIG. 2A is a diagram projecting the trajectory of the probe unit 110 onto the XY plane. In Embodiment 1, the object is irradiated with the pulsed light at predetermining timings (Te1, Te2, Te3, . . . , TeN), and volume data (V1, V2, . . . , VN) is generated based on the received acoustic wave. In FIG. 2A, Pos1, Pos2 and Pos3 indicate the center positions of the high resolution region at the pulsed light irradiation timings Te1, Te2 and Te3. In the case of the probe unit having the hemispheric support member, as in the case of Embodiment 1, Pos1, Pos2 and Pos3 can be regarded as positions when the center of this hemisphere is projected onto the XY plane. Each dotted line centering around each point of Pos1, Pos2 and Pos3 is a schematic representation of the spread of the high resolution region at each position.

In Embodiment 1, a plurality of positions where the high resolution regions overlap is irradiated with the pulsed light, and the acoustic wave is received and the photoacoustic signal is acquired at these positions. In the high resolution region, high directivity regions of the plurality of conversion elements 101 overlap, and the photoacoustic signal generated in this region can be acquired at a high SN ratio. Further, the photoacoustic signals are acquired while changing the relative position of the probe unit 110 with respect to the object, hence the generation of an artifact in the reconstructed image can be suppressed. In Embodiment 1, the region on the object where the object is irradiated with the pulsed light (light irradiation region) is a position corresponding to the center of the high resolution region. The pulsed light irradiation region also moves with the high resolution region as the probe unit 110 moves. In other words, the optical system 104 is configured to irradiate the object in different irradiation positions along a rotational trajectory during a rotational scanning period of time in a corresponding wavelength.

Operation of the data processing unit 106 will be described next.

First the image generating unit 1061 executes the image reconstruction based on the photoacoustic signals outputted from the signal acquiring unit 105, and outputs volume data. This image reconstruction is performed independently for the photoacoustic signal acquired at each irradiation of the pulsed light.

Then the image processing unit 1062 combines a plurality of photoacoustic volumes so as to generate a composite volume in which an artifact is suppressed. In the following, the volume data and composite data are also called "image data" and "composite image data" respectively.

In the example in FIG. 2A and FIG. 2B, the object is irradiated with the pulsed light at a timing when the center of the high resolution region is located at Pos1, and using the photoacoustic signal acquired thereby, an image is reconstructed for the space including the high resolution region centering around Pos1 indicated by the dotted line, and the volume data V1 is acquired as a result.

Then the object is irradiated with the pulsed light at a timing when the center of the high resolution region is located at Pos2, and using the photoacoustic signal acquired thereby, an image is reconstructed for the space including the region centering around Pos2 indicated by the dotted line, and the volume data V2 is acquired as a result. In the same manner, when the center of the high resolution region is located at Pos3 and Pos4, the volume data V3 and the volume data V4 are acquired respectively.

The image processing unit 1062 combines these four volume data while maintaining the relative positional relationships thereof, and calculates the composite volume data V'1. Thereby in a region where with each volume data overlaps, a photoacoustic image, in which an artifact is suppressed, can be acquired. In order to implement this effect, it is preferable that the distance L between at least two locations, out of the locations of the center point of the high resolution region when the object is irradiated with the pulsed light, is smaller than the radius R of the high resolution region.

Further, by controlling the movement of the probe unit 110 so that the high resolution regions overlap regardless of which position of the trajectory the probe unit 110 is located, the image can be reconstructed using more photoacoustic signals. In other words, a photoacoustic image in which an artifact is further suppressed can be acquired. For example, this effect can be implemented by controlling $R_{rot}$, which is the radius of the trajectory 201, becomes smaller than the radius R of the high resolution region.

If $R_{rot}$ is controlled to be $R_{rot} < R/2$, then the high resolution regions can be overlapped in all the regions inside the rotational trajectory. In other words, a photoacoustic image, in which an artifact is suppressed in an even wider range, can be acquired.

In Embodiment 1, as illustrated in FIG. 2B, the object is irradiated with the pulsed light at equal intervals while changing the position of the probe unit 110 to Pos1, Pos2, Pos3, . . . , PosN. When the photoacoustic signal is acquired at each timing, the image generating unit 1061 reconstructs the image, and generates the volume data V1, V2, . . . , VN. Then the image processing unit 1062 generates the composite volume data V'1 using the four volume data V1 to V4. In this example, the composite volume data V'n is generated by combining the volume data Vn to V(n+3).

The image corresponding to the composite volume data acquired like this is sequentially outputted to the display device 107. Thereby a photoacoustic image, which is updated in real-time, can be provided. The volume data is generated by receiving the photoacoustic waves at positions where the high resolution regions overlap with each other, hence an artifact near the overlapped positions in particular can be suppressed.

The composite volume data is acquired by combining photoacoustic signals corresponding to a plurality of times of pulsed light irradiation. However, in the case where the object is a living body, the imaging target may move due to body motion (e.g. breathing), and in this case, blur may be generated due to the body motion if the composite volume data is generated by combining the photoacoustic signals acquired before and after the body motion.

Therefore, it is preferable to limit a number of volume data to be combined to a number which is not subject to the influence of the body motion. For example, if the body motion caused by breathing is about 0.3 Hz (about a 3.33 second cycle), the photoacoustic signals acquired during a period shorter than this cycle are combined, then an image which is less affected by the body motion can be acquired.

If the cycle of the pulsed light irradiation is 10 Hz, a number of volume data to be combined may be limited to 16 at the maximum, then the photoacoustic signals used for the combining can be acquired within 1.6 seconds, and the combining can be performed within about half of the body motion cycle. If a number of volume data to be used for the combining is limited to 8 at the maximum, the photoacoustic signals to be combined can be acquired within 0.8 seconds, hence the combining can be performed in about ¼ of the body motion cycle. As a number of volume data to be combined decreases, an image having the higher time resolution can be acquired, and as a number of volume data to be combined increases, an image having a higher SN ratio can be acquired.

A number of volume data to be combined may be arbitrarily set by the operator. Further, if a number of volume data to be combined and displayed, operational convenience for the operator can be enhanced. Furthermore, if the acquiring time duration to acquire the photoacoustic signals to be combined or a cycle (Hz) calculated based on the acquiring time duration are displayed, the operator can recognize the time resolution of the acquired image. This makes it easier for the operator to specify a number of volume data to be combined and a time resolution.

According to the above-mentioned operation, the photoacoustic signal acquired at timing Te2 is reflected in the images Im1 and Im2, but not in image Im3. The photoacoustic signal acquired at timing Te3 is reflected in images Im1, Im2 and Im3, but not in image Im4. In other words, the degree of contribution of a photoacoustic signal acquired at a certain timing (or volume data using this photoacoustic signal) in the display image decreases as time elapses. As a result, an artifact can be suppressed by combining the volume data, and the image can be updated while suppressing the contribution of an older photoacoustic signal in the image.

An overview on the above-mentioned operation will be described next.

In Embodiment 1, a photoacoustic signal is acquired at each position of N locations (n is 3 or greater integer), of which relative position with respect to the object is different respectively, whereby N number of volume data are acquired. Then a first composite volume data is generated by combining at least two volume data out of the ith to (i+m)th volume data (i+m<N, both i and m are natural numbers). Further, a second composite volume data is generated by combining at least two volume data out of (i+n)th to (i+n+m)th volume data (n is a natural number). Then the image based on the first composite volume data is updated to an image based on the second composite volume, whereby the first composite image and the second composite image are sequentially displayed.

As illustrated in FIG. 2A, photoacoustic signals are received while repeatedly circling around a predetermined region (e.g. center of trajectory 201), and the image acquired by combining a plurality of volume data is displayed periodically, whereby a moving image corresponding to the predetermined region can be provided. This moving image may be outputted to the display device 107, or may be stored in a storage unit (not illustrated).

When the composite volume data is created from volume data, the ratio of combining each volume data may be weighted in order to decrease the degree of contribution of an older photoacoustic signal. For example, in the case when composite volume data is created using volume data V(i) to V(i+m), and the ratio of each volume is α(i) to α(i+m), then $\alpha(i) \leq \alpha(i+1) \leq \alpha(i+2) \leq \alpha(i+3) \ldots \leq \alpha(i+m)$ is satisfied. Thereby the contribution of an older photoacoustic signal to the composite volume data can be further reduced.

Further, the time duration required to acquire the volume data (e.g. period from the timing when the photoacoustic signal corresponding to Pos1 is acquired to the timing when the photoacoustic signal corresponding to Pos4 is acquired) may be displayed on the display device 107. Then the operator can grasp a general idea of the time resolution of the currently displayed composite image data.

Furthermore, the values of the ratio of each volume ($\alpha(i)$ to $\alpha(i+m)$) to create the composite volume data may be displayed. These values may be changed by the operator. Then the operator can adjust the measurement parameters in accordance with the desired time resolution and artifact suppression level.

The image processing unit 1062 may perform image processing to emphasize a region corresponding to the high resolution region on the image, so as to differentiate this region from the other regions.

Embodiment 1 can also be applied to the case of using a light source, that can irradiate the object with a plurality of pulsed lights having different wavelengths. For example, in the case of switching the wavelength of the pulsed light each time the object is irradiated with the pulsed light, an image may be reconstructed using the photoacoustic signals acquired when the object is irradiated with the pulsed lights having different wavelengths, or an image may be reconstructed using the photoacoustic signals acquired when the object is irradiated with the pulsed lights having the same wavelength. In either case, it is preferable that at least two of the high resolution regions where the photoacoustic signals were acquired at a plurality of timings, overlap. If only the photoacoustic signals acquired by irradiating the object with the pulsed lights having the same wavelength are used, a photoacoustic image unique to this wavelength can be acquired with less artifacts. In the case of using a plurality of photoacoustic signals corresponding to the same wavelength, it is preferable to use the photoacoustic signals of which acquired timings are close to each other, then a photoacoustic image having a high time resolution can be acquired.

A case of irradiating the object with pulsed lights having different wavelengths and generating an image on functional information inside the object, based on the acquired photoacoustic signals, will be described next.

Figure 3:
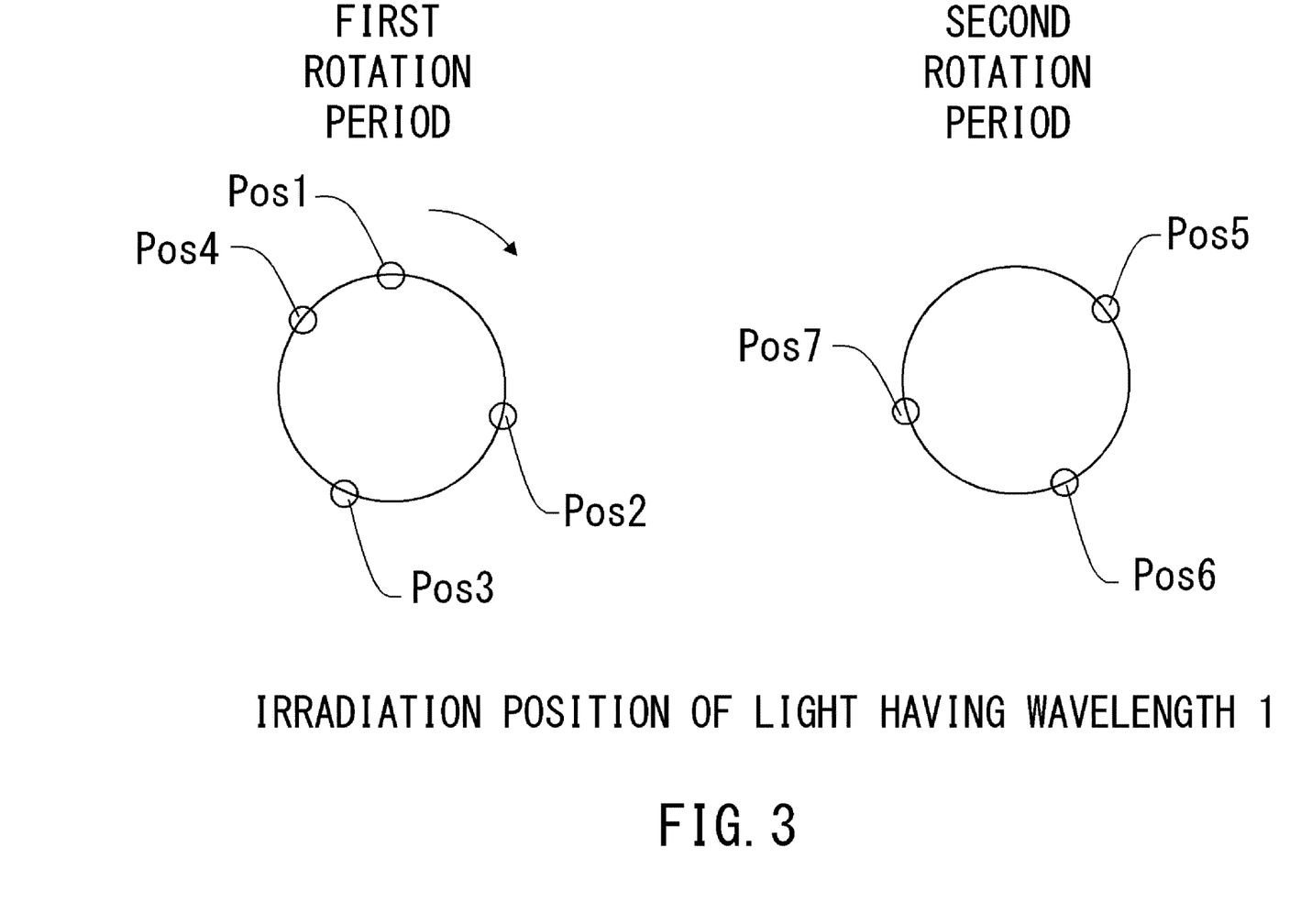
FIG. 3 indicates diagrams depicting a center position of a high resolution region at each irradiation timing.
Figure 4:
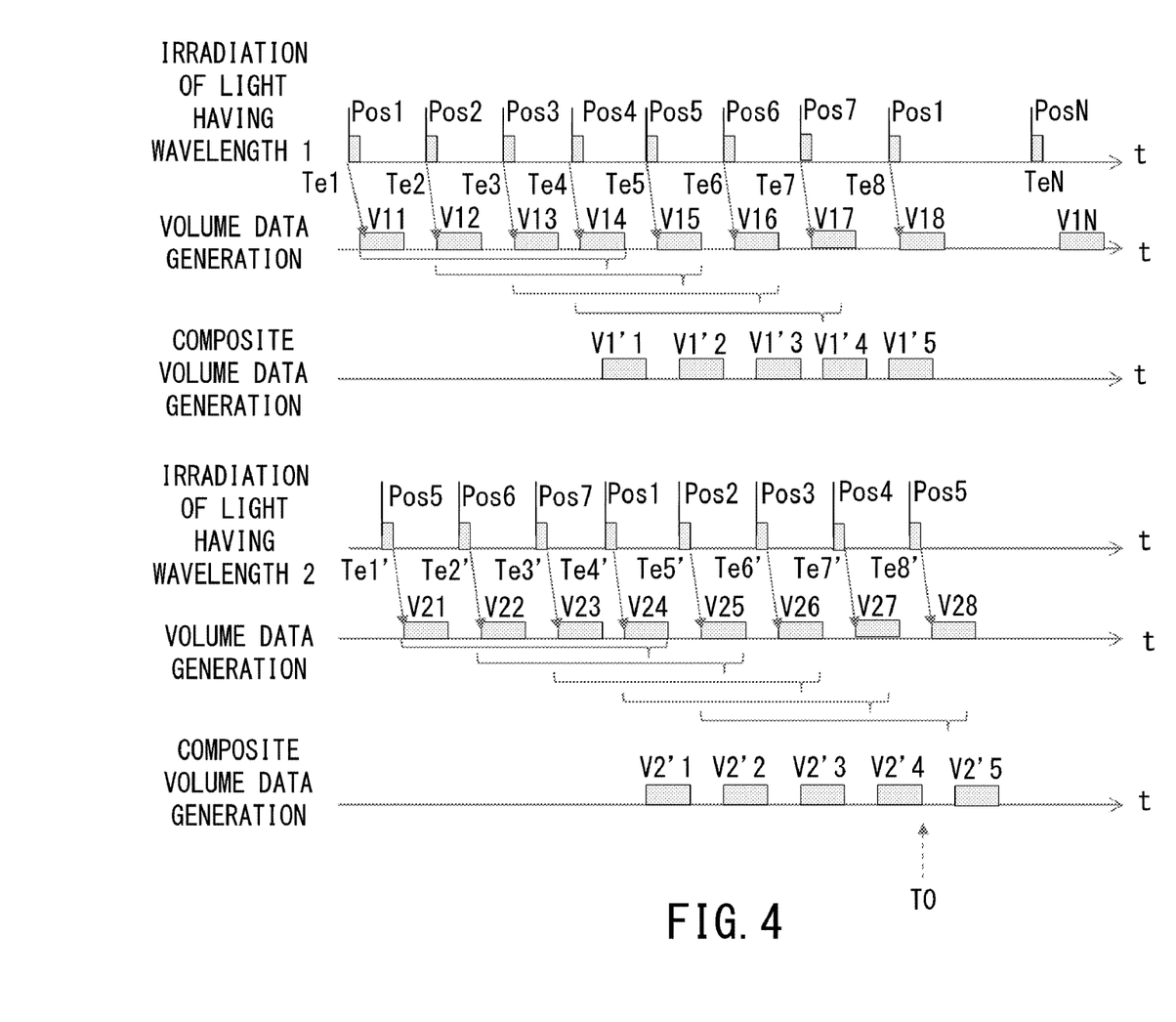
FIG. 4 indicates diagrams depicting irradiation timings at each wavelength according to Embodiment 1.

FIG. 3 indicates schematic diagrams depicting a center position of a high resolution region at each light irradiation timing. In this example, the center position of the high resolution region changes clockwise. FIG. 4 indicates diagrams depicting irradiation timings at each wave length.

The photoacoustic apparatus according to Embodiment 1 irradiates the object with a pulsed light having wavelength 1 and a light having wavelength 2 alternately while rotating the probe unit 110.

First the pulsed light irradiation timing will be described, focusing on the pulsed light having wavelength 1.

In the first rotation, the object is irradiated with the pulsed light having wavelength 1 at the timings Te1, Te2, Te3 and Te4 respectively. The center position of the high resolution region (light irradiation position, that is, a position where the center of the hemisphere is projected to the XY plane) at each timing is Pos1, Pos2, Pos3 and Pos4 respectively. In the second rotation, the object is irradiated with the pulsed light having wavelength 1 at the timings Te5, Te6 and Te7 respectively. The center position of the high resolution region (light irradiation position) at each timing is Pos5, Pos6 and Pos7 respectively.

In the first rotation, the object, on the other hand, is irradiated with the pulsed light having wavelength 2 at the timings Te1', Te2' and Te3' respectively. The center position of the high resolution region (light irradiation position) at each timing is Pos5, Pos6 and Pos7 respectively. In the second rotation, the object is irradiated with the pulsed light having wavelength 2 at the timings Te4', Te5', Te6' and Te7' respectively. The center position of the high resolution region (light irradiation position) at each timing is Pos1, Pos2, Pos3 and Pos4 respectively.

In this way, the photoacoustic apparatus according to Embodiment 1 controls so that the irradiation positions of the pulsed light having wavelength 1 in the first rotation become the same as the irradiation positions of the pulsed light having wavelength 2 in the second rotation (Pos1, Pos2, Pos3 and Pos4). Further, the photoacoustic apparatus according to Embodiment 1 controls so that the irradiation positions of the pulsed light having wavelength 2 in the first rotation become the same as the irradiation positions of the pulsed light having wavelength 1 in the second rotation (Pos5, Pos6 and Pos7). In other words, the control is performed so that the same positions on the object are irradiated with pulsed lights having different wavelengths in different rotations.

Description continues with reference to FIG. 4.

Volume data V11 is acquired by the photoacoustic signal acquired by irradiating the object with the pulsed light having wavelength 1 to Pos1. Volume data V12 is acquired by the photoacoustic signal acquired by irradiating the object with the pulsed light having wavelength 1 to Pos2. Composite volume data V1'1 is acquired by combining the volume data V11, V12, V13 and V14. Composite volume data V1'2 is acquired by combining the volume data V12, V13, V14 and V15.

This is also the same for the pulsed light having wavelength 2.

In other words, volume data V21, V22, V32, . . . are acquired from the photoacoustic signals acquired by irradiating the object with the pulsed light having wavelength 2 to Pos5, Pos6, Pos7, . . . . Then composite volume data V2'1 is acquired by combining the volume data V21, V22, V23 and V24. Further, composite volume data V2'2 is acquired by combining the volume data V22, V23, V24 and V25.

Next description focuses on the composite volume data V1'1 and the composite volume data V2'4. The composite volume data V1'1 is generated by combining the volume data V11, V12, V13 and V14, and each volume data is based on the data acquired when the center of the high resolution region is at the positions Pos1, Pos2, Pos3 and Pos4 respectively. The composite volume data V2'4 is generated by combining the volume data V24, V25, V26 and V27, and each volume data is based on the data acquired when the center of the high resolution region is at the positions Pos1, Pos2, Pos3 and Pos4 respectively. In other words, the composite volume data V1'1 and the composite data V2'4 are generated using the photoacoustic signals acquired by irradiating the same positions on the object with the pulsed light. This means that the functional information volume can be calculated by using this data.

Here an example of calculating an index on the oxygen saturation degree from the volume data using the photoacoustic signals corresponding to pulsed lights having different wavelengths will be described.

The oxygen saturation degree (SO2) can be calculated by the following formula (2).

In formula (2), [HbO$_2$] is a concentration of oxyhemoglobin, and [Hb] is a concentration of deoxyhemoglobin. $\varepsilon Hb\lambda_1$ and $\varepsilon Hb\lambda_2$ are the molar absorption coefficients of deoxyhemoglobin at wavelengths $\lambda_1$ and $\lambda_2$ respectively, and $\Delta\varepsilon Hb\lambda_1$ and $\Delta\varepsilon Hb\lambda_2$ are values determined by subtracting the molar absorption coefficients of the deoxyhemoglobin from the molar absorption coefficients of the oxyhemoglobin at wavelengths $\lambda_1$ and $\lambda_2$ respectively. The absorption coefficients ($\mu_a\lambda_1$ and $\mu_a\lambda_2$) are the absorption coefficients at the wavelengths $\lambda_1$ and $\lambda_2$ respectively at each position, and are acquired by dividing the initial sound pressure distribution acquired as the composite volume by optical fluence.

[Math. 2]

$$SO_2 = \frac{[HbO_2]}{[HbO_2] + [Hb]} = \frac{\mu_a^{\lambda 2}\varepsilon_{Hb}^{\lambda 1} - \mu_a^{\lambda 1}\varepsilon_{Hb}^{\lambda 2}}{\mu_a^{\lambda 1}\Delta\varepsilon_{Hb}^{\lambda 2} - \mu_a^{\lambda 2}\Delta\varepsilon_{Hb}^{\lambda 1}} = \frac{\phi_{\lambda 1}/\phi_{\lambda 2}P^{\lambda 2}\varepsilon_{Hb}^{\lambda 1} - P^{\lambda 1}\varepsilon_{Hb}^{\lambda 2}}{\phi_{\lambda 2}/\phi_{\lambda 1}P^{\lambda 1}\Delta\varepsilon_{HB}^{\lambda 2} - P^{\lambda 2}\Delta\varepsilon_{Hb}^{\lambda 1}} \quad \text{Formula (2)}$$

Here the operation timing of the image processing unit 1062 will be described. As mentioned above, in order to acquire a highly accurate functional information volume, it is necessary to wait until the composite volume data V1'1 and the composite volume data V2'4 are acquired. Therefore, to display the functional information volume while imaging is performed, it is preferable to start operation and update the display at the point when the positions on the object which are irradiated with pulsed lights having different wavelengths in different rotations overlap, and an instructed number of volume data are acquired (e.g. timing T0 in FIG. 4).

Until the timing T0 is reached, the functional information volume may be calculated using a composite volume data combining volume data acquired at close timings, such as the composite volume data V2'1 and the composite volume data V1'1.

Further, the functional information volume may be calculated using each volume data before generating the composite volume data. By starting processing at this timing, the operator can check at an early timing whether or not imaging started.

The effect of Embodiment 1 will be described next with reference to FIG. 5A to FIG. 5J.

FIG. 5A to FIG. 5G are diagrams depicting a pulsed light irradiation distribution at each position corresponding to Pos1 to Pos7. The circle in each diagram indicates a center of the high sensitivity region. For example, in the case where each position of Pos1, Pos2, Pos3 and Pos4 on the object is irradiated with the pulsed light having wavelength 1 in the first rotation, the photoacoustic signal corresponding to each pulsed light irradiation distribution indicated in FIG. 5A to FIG. 5D is acquired.

In the case where each position of Pos1, Pos2, Pos3 and Pos4 on the object is irradiated with the pulsed light having wavelength 2 at the timings Te4', Te5', Te6' and Te7' in the second rotation as well, the photoacoustic signal corresponding to each pulsed light irradiation distribution indicated in FIG. 5A to FIG. 5D is acquired.

Figure 5A:
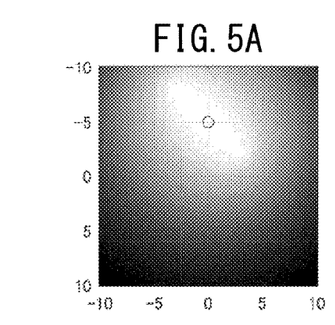
FIG. 5A to FIG. 5J indicate diagrams depicting the pulsed light irradiation distribution according to Embodiment 1.
Figure 5B:
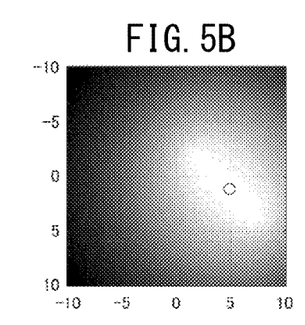
Figure 5C:
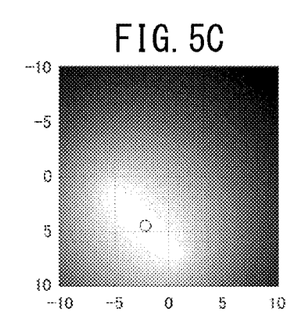
Figure 5D:
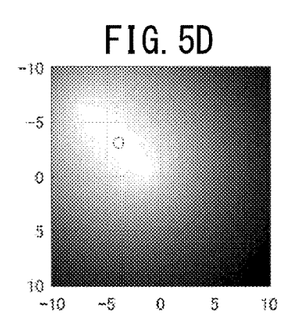
Figure 5E:
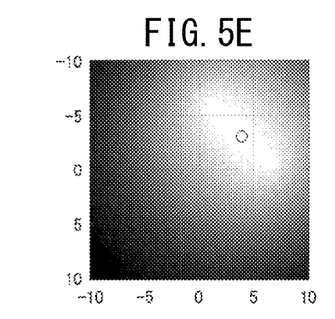
Figure 5F:
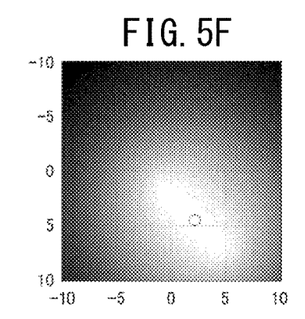
Figure 5G:
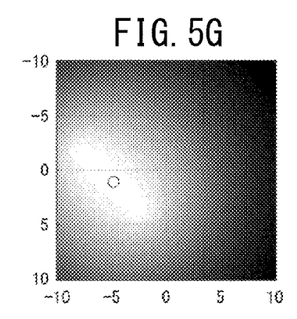
Figure 5H:
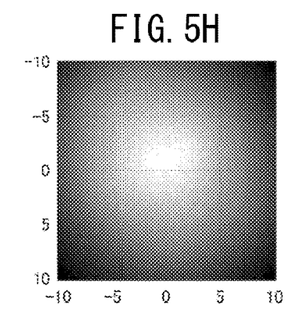

By combining volume data calculated from each photoacoustic signal acquired like this, the composite volume data is acquired. In other words, the composite volume data V1'1 corresponding to the wavelength 1 and the composite volume data V2'4 corresponding to the wavelength 2 are both equivalent to an image reconstructed using the photoacoustic signals generated based on the pulsed light irradiation distribution integrating the four pulsed light irradiation distributions. FIG. 5H is generated by integrating the pulsed light irradiation distributions in FIG. 5A, FIG. 5B, FIG. 5C and FIG. 5D.

However as indicated in formula (2), the optical fluence ratio of the two wavelengths is included in the calculation formula to determine the oxygen saturation degree. Therefore, if the pulsed light irradiation distribution is different depending on the wavelength in the region of interest, error may be increased, including an increase in the load of the correction processing when the oxygen saturation degree is calculated.

Figure 5I:
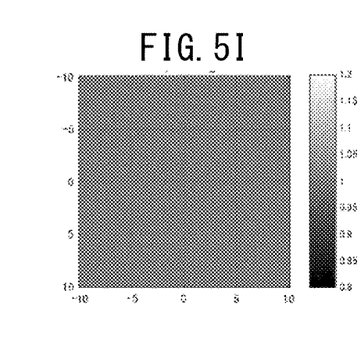

In the case of the photoacoustic apparatus according to Embodiment 1, on the other hand, the functional information volume, such as the oxygen saturation degree, is calculated using the composite volume data V1'1 and the composite volume data V2'4. Both of these composite volumes use the photoacoustic signals acquired by irradiating a same position on the object with the pulsed lights, hence the pulsed light irradiation distribution ratio at each wavelength is uniform, as indicated in FIG. 5I.

Figure 5J:
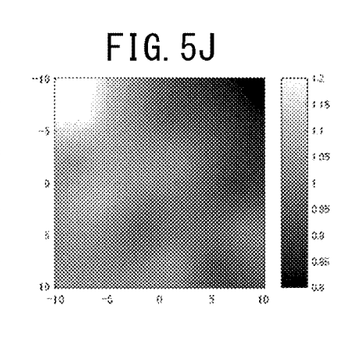

If the pulsed light irradiation positions are different depending on the wavelength, on the other hand, highly accurate information cannot be acquired since the pulsed light irradiation distribution ratio varies at each wavelength. FIG. 5J indicates the pulsed light irradiation distribution ratio when the oxygen saturation degree is calculated using the composite volume acquired by irradiating Pos1, Pos2, Pos3 and Pos4 on the object with the pulsed light having wavelength 1, and the composite volume acquired by irradiating Pos5, Posh, Pos7 and Pos1 on the object with the pulsed light having wavelength 2. As FIG. 5J indicates, if the above-mentioned control is not performed, the pulsed light irradiation distribution ratio varies when the object is irradiated with the pulsed lights having a plurality of wavelengths, which drops accuracy.

As described above, in the photoacoustic apparatus according to Embodiment 1, control is performed so that the positions on the object which are irradiated with the pulsed light having the first wavelength in the first rotation and the positions on the object which are irradiated with the pulsed light having the second wavelength in the second rotation, which is performed after the first rotation, overlap. In other words, the control is performed so that the positions on the object which are irradiated with the pulsed lights having different wavelengths overlap at different timings. Thereby the accuracy when the functional information volume is calculated can be improved.

If a number of volume data to be combined (hereafter "averaging number") is increased, the pulsed light irradiation distribution in the region of interest is equalized. The averaging number is preferably about a number of times of irradiating the object with a pulsed light having a wavelength in one rotation (e.g. about 3 to 4 times in the example of FIG. 3). Unless otherwise specified, a number of times of irradiation during one rotation may be used as the default value of the averaging number.

Embodiment 2

A photoacoustic apparatus according to Embodiment 2 will be described next with reference to FIG. 6. A difference of the photoacoustic apparatus according to Embodiment 2 from Embodiment 1 is the control method of calculating the composite volume in the image processing unit 1062. Embodiment 2 thereafter is the same as Embodiment 1, except for this control method, hence redundant description will be omitted.

In Embodiment 1, the averaging number to generate the composite volume data is 4. In Embodiment 2, the averaging number is a number of times of irradiation until an irradiation position of a pulsed light having a certain wavelength returns to the same irradiation position in a plurality of rotations (this averaging number is 7 in the example of FIG. 3).

Figure 6:
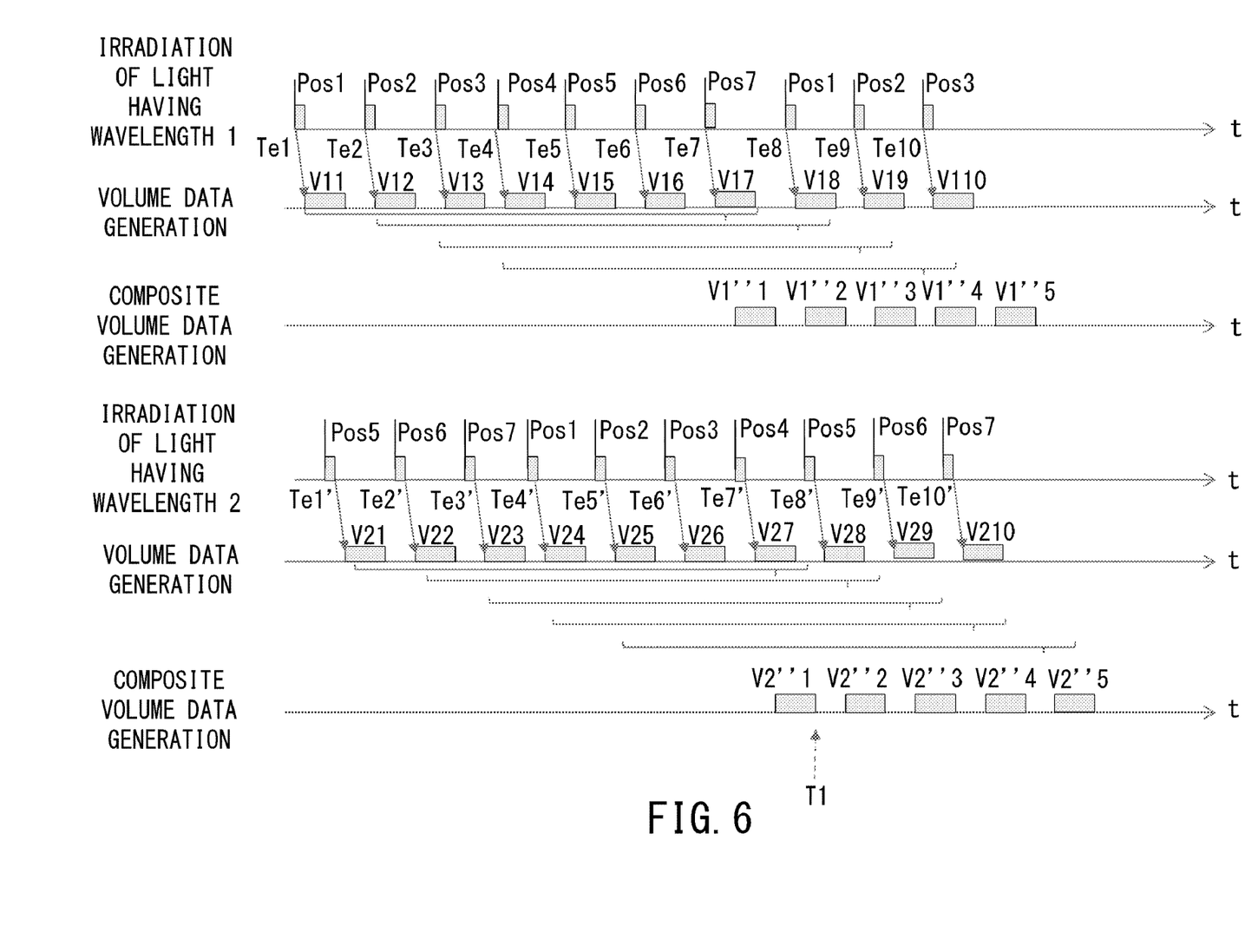
FIG. 6 indicates diagrams depicting irradiation timings at each wavelength according to Embodiment 2.

FIG. 6 indicates diagrams depicting irradiation timings according to Embodiment 2. As illustrated, in Embodiment 2, seven volume data of volume data V11 to V17 acquired by a plurality of times of rotation, are combined, so as to generate a composite volume data V1"1 corresponding to the wavelength 1. In the same manner, 7 volume data of volume data V21 to V27 acquired by a plurality of times of rotation, are combined, so as to generate a composite volume data V2"1 corresponding to the wavelength 2.

This composite volume includes all photoacoustic signals acquired by irradiating Pos1, Pos2, Pos3, Pos4, Posy, Pos6 and Pos7 with pulsed lights, although the acquiring sequence is different. Therefore, the pulsed light irradiation distribution ratio among different wavelengths becomes more uniform. In Embodiment 2, calculation of the functional information volume can be started at the timing T1 indicated in FIG. 6.

In this way, according to Embodiment 2, a number of times of irradiation of pulsed light having a certain wavelength in one rotation, from a first irradiation position back to the same irradiation position (7 times in this example), is used as the average number. Thereby variation of the pulsed light irradiation distribution ratio between different wavelengths can be suppressed, and accuracy of the functional information volume can be improved. Further, a moving image with very little flicker can be displayed, because images using the photoacoustic signals, which are acquired based on the same pulsed light irradiation distribution, can be sequentially updated.

Modification

The description on the embodiments are merely examples to describe the present invention, and the present invention can be carried out by appropriately changing or combining the above embodiments within a scope that does not depart from the spirit of the invention.

For example, the present invention may be carried out as a photoacoustic apparatus which includes at least a part of the above-mentioned units. Further, the present invention may be carried out as an object information acquiring method which includes at least a part of the above-mentioned processing. These processing and units may be freely combined as long as no technical inconsistency is generated.

In the description of the embodiments, the pulsed light irradiation positions overlap, but the pulsed light irradiation distributions need not perfectly match, and it is sufficient if the center or the center of gravity position of the pulsed light irradiation distribution corresponding to each wavelength exists close to each other. The effect of the present invention is implemented if the distance of the irradiation positions between pulsed lights having different wavelengths in different rotations is shorter than the distance between the irradiation positions between pulsed light with different wavelengths in a same rotation (e.g. distance between Pos1 at timing Te1 and Pos5 at timing Te1').

In the description of the embodiments, positions determined by dividing one cycle of the rotating motion by 7 are irradiated with pulsed light, using two different wavelengths, but in the case of using two different wavelengths, the effect of the present invention is implemented if one cycle is divided into 2N+1 (N is a natural number), and each position on the object is irradiated with two pulsed lights having different wavelengths alternately.

In the case of irradiating the object with pulsed lights having three different wavelengths with sequentially switching, the effect of the present invention is implemented if one cycle is divided into 3N+1 or 3N−1 (N is a natural number).

In each of the above cases, a number of times of irradiation of one wavelength per rotation is the floor function ((2N+1)/2) if two wavelengths are used, and is the floor function ((3N±1)/3) if three wavelengths are used, since these numbers may be used as a default averaging number.

In the description of the embodiments, a case of two or three wavelengths was used as an example, but more wavelengths may be used. The effect of the present invention can be implemented if at least two of these wavelengths are controlled to irradiate the same positions with the pulsed light in different rotations.

Further, a number of wavelengths and an average number to be used may be automatically determined by the system with reference to information attached to the inspection information inputted to the system, or may be values set by the user in advance.

The control parameters used by the photoacoustic apparatus may be set or changed based on input by the operator or the information attached to the inspection information. For example, if the operator instructed or if it is determined based on the information attached to the inspection information that the time resolution must be improved, then a frequency of the light source, a number of times of pulsed light irradiation per rotation, a time required for one rotation, a radius of rotating motion, a number of times of averaging and the like may be changed.

In the description of the embodiments, the conversion elements and the end of the irradiation optical system are integrated as an example, but the present invention is not limited to this example. Further, in the description of the embodiments, irradiation of light and receiving of the acoustic wave are performed in parallel with the generation of an image, but the present invention is not limited to this example.

The present invention may be implemented by executing the following processing. That is, a program to implement at least one function of the above-mentioned embodiments is supplied to a system or apparatus via a network or various storage media, and at least one processor of the computer of the system or apparatus reads and executes the program. The present invention may also be implemented by a circuit (e.g. ASIC, FPGA), which implements at least one function of the above embodiments.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-081436, filed on Apr. 20, 2018, which is hereby incorporated by reference herein in its entirety.

What is claimed is:

1. A photoacoustic apparatus comprising:
a light irradiation unit optically coupled to a light source configured to generate a plurality of first pulsed lights in a first wavelength and a plurality of second pulsed lights in a second wavelength different from the first wavelength alternatively and configured to irradiate an object with the plurality of first pulsed lights and the plurality of second pulsed lights alternatively;
a scanning unit configured to move the light irradiation unit with respect to the object in a circulating manner in a common circulating path repeatedly;
a probe configured to receive a plurality of acoustic waves from the object in response to the first and second pulsed light irradiations from the light irradiation unit and to output a plurality of first reception signals in association with the plurality of first pulsed lights and a plurality of second reception signals in association with the plurality of second pulsed lights;
an image processing unit configured to perform image processing including a processing of an image reconstruction to generate a plurality of photoacoustic image data based on the plurality of first and second reception signals and a processing of combining the plurality of the photoacoustic image data to generate a composite volume data; and
a control unit configured to control an irradiation timing, an irradiation position and the first and second wavelengths of the first and second pulsed lights from the light source,
wherein the image processing unit is configured to generate a first composite volume data based on a group of the first reception signals, in which a number of signals are in association with predetermined averaging numbers, out of the plurality of the first reception signals intermittently obtained from the probe and a second composite volume data based on a group of the second reception signals, in which a number of signals are in association with the predetermined averaging numbers, out of the plurality of second reception signals intermittently obtained from the probe, and
wherein the control unit is configured to control a first group of the irradiation positions in the common circulating path in association with the group of first reception signals in a certain circulating period to be in accordance with a second group of the irradiation positions in the common circulating path in association with the group of second reception signals in a different circulating period different from the certain circulating period in timing.

2. The photoacoustic apparatus according to claim 1, further comprising:
an image generating unit configured to generate a first image data based on a first reception signal in association with the first pulsed lights in the first wavelength and generate a second image data based on a second reception signal in association with the second pulsed lights in the second wavelength.

3. The photoacoustic apparatus according to claim 2, wherein the image generating unit is configured to generate the first image data and the second image data in parallel with irradiation of the first pulsed lights and the second pulsed lights and reception of a first acoustic wave and a second acoustic wave.

4. The photoacoustic apparatus according to claim 2, wherein the image generating unit generates a third image data which expresses a functional information in the object based on a common irradiated region in association with the first image data and the second image data.

5. The photoacoustic apparatus according to claim 4, wherein the image generating unit is configured to update the third image data in response to both of an update of the first image data and an update of the second image data in association with the common irradiated region.

6. The photoacoustic apparatus according to claim 4, wherein the third image data includes an image data generated based on an oxygen saturation degree of the object.

7. The photoacoustic apparatus according to claim 1, further comprising a support member configured to support the light irradiation unit and the probe such that the light irradiation unit and the probe are configured as a unit.

8. The photoacoustic apparatus according to claim 1, wherein the control unit switches the first wavelength and the second wavelength alternately.

9. The photoacoustic apparatus according to claim 1, wherein the scanning unit moves the light irradiation unit and the probe integrally with respect to the object.

10. The photoacoustic apparatus according to claim 1, wherein the plurality of acoustic waves includes a plurality of photoacoustic waves generated in response to the first pulsed lights or the second pulsed lights from the light irradiation unit.

11. A method of acquiring object information comprising:
   irradiating an object with a plurality of first pulsed lights in a first wavelength and a plurality of second pulsed lights in a second wavelength different from the first wavelength alternatively emitted from a light irradiation unit moving with respect to the object in a circulating manner in a common circulating path;
   moving the light irradiation unit with respect to the object in the circulating manner in the common circulating path repeatedly;
   receiving acoustic wave from the object in response to light irradiation in different irradiation positions;
   outputting a plurality of first reception signals in association with the plurality of first pulsed lights and a plurality of second reception signals in association with the plurality of second pulsed lights;
   performing image processing including a processing of an image reconstruction to generate a plurality of photoacoustic image data based on the plurality of first and second reception signals and a processing of combining the plurality of the photoacoustic image data to generate a composite volume data; and
   controlling an irradiation timing, an irradiation position and the first and second wavelengths of the first and second pulsed lights from a light source,
   wherein the image processing is performed such that a first composite volume data based on a group of the first reception signals, in which a number of signals are in association with predetermined averaging numbers, out of the plurality of the first reception signals intermittently obtained from a probe is generated and a second composite volume data based on a group of the second reception signals, in which a number of signals are in association with the predetermined averaging numbers, out of the plurality of the second reception signals intermittently obtained from the probe is generated, and
   wherein the controlling is performed such that a first group of the irradiation positions in the common circulating path in association with the group of the first reception signals in a certain circulating period is in accordance with a second group of the irradiation positions in the common circulating path in association with the group of second reception signals in a different circulating period different from the certain circulating period in timing.

12. The method of acquiring object information according to claim 11, further comprising:
   generating a first image data based on a first reception signal in association with the first pulsed lights in the first wavelength; and
   generating a second image data based on a second reception signal in association with the second pulsed lights in the second wavelength.

13. The method of acquiring object information according to claim 12, wherein the generating generates the first image data and the second image data in parallel with any irradiation of the pulsed light and any reception of the acoustic wave.

14. The method of acquiring object information according to claim 12, wherein the image processing is performed such that a third image data indicating functional information in the object is to be generated based on the first image data and the second image data in association with a common irradiated region which is irradiated with both of the first pulsed lights and the second pulsed lights.

15. The method of acquiring object information according to claim 14, wherein the generating updates the third image data in response to both of an update of the first image data and an update of the second image data in association with the common irradiated region.

16. The method of acquiring object information according to claim 14, wherein the third image data includes an image data generated based on an oxygen saturation degree of the object.

17. The method of acquiring object information according to claim 11, wherein the irradiating is performed such that the wavelength of any one of the first pulsed lights and the second pulsed lights is to be changed.

18. The method of acquiring object information according to claim 11, wherein the acoustic wave includes a photoacoustic wave generated in response to the first pulsed lights or the second pulsed lights from the light irradiation unit.

19. The method of acquiring object information according to claim 11, further comprising:
   controlling at least any one of the irradiation timing of the light irradiation, the first wavelength, the second wavelength, and the irradiation position of the light irradiation unit on the object.

20. The method of acquiring object information according to claim 11, wherein the irradiating and the receiving are performed such that the light irradiation unit and a probe configured to receive acoustic wave are moved integrally with respect to the object.

* * * * *